(12) United States Patent
Dohi et al.

(10) Patent No.: US 6,626,828 B2
(45) Date of Patent: Sep. 30, 2003

(54) BODY CAVITY-OBSERVING APPARATUS

(75) Inventors: Takeyoshi Dohi, Tokyo (JP); Ichiro Sakuma, Yokohama (JP); Etsuko Kobayashi, Tokyo (JP); Makoto Iwahara, Yokohama (JP)

(73) Assignee: The University of Tokyo, Tokyo (JP)

( * ) Notice: Subject to any disclaimer, the term of this patent is extended or adjusted under 35 U.S.C. 154(b) by 23 days.

(21) Appl. No.: 09/883,603

(22) Filed: Jun. 18, 2001

(65) Prior Publication Data

US 2002/0022767 A1 Feb. 21, 2002

(30) Foreign Application Priority Data

Jun. 20, 2000 (JP) ........................................ 2000-184607

(51) Int. Cl.[7] ................................................ A61B 1/00
(52) U.S. Cl. ........................ 600/173; 600/176; 600/171
(58) Field of Search .................................. 600/173, 175, 600/176, 171; 359/831, 832, 837

(56) References Cited

U.S. PATENT DOCUMENTS

| 3,229,577 | A | | 1/1966 | Henry | |
|---|---|---|---|---|---|
| 3,856,000 | A | * | 12/1974 | Chikama | 600/173 |
| 3,880,148 | A | * | 4/1975 | Kanehira et al. | 600/173 |
| 4,398,811 | A | * | 8/1983 | Nishioka et al. | 359/367 |
| 4,697,577 | A | * | 10/1987 | Forkner | 600/173 |
| 4,717,823 | A | * | 1/1988 | Steimel et al. | 250/236 |
| 4,870,950 | A | | 10/1989 | Shimizu et al. | |
| 5,133,035 | A | * | 7/1992 | Hicks | 385/117 |
| 5,184,602 | A | | 2/1993 | Anapoliotis et al. | |
| 5,700,236 | A | | 12/1997 | Greenwald et al. | |
| 5,754,339 | A | * | 5/1998 | Kanai et al. | 359/557 |
| 5,862,001 | A | * | 1/1999 | Sigler | 359/832 |
| 6,371,909 | B1 | * | 4/2002 | Hoeg et al. | 600/173 |

FOREIGN PATENT DOCUMENTS

| EP | 0 260 856 A | 3/1988 |
|---|---|---|
| JP | 06237881 A | 8/1994 |
| JP | 8-164148 | 6/1996 |
| JP | 10174673 A | 6/1998 |
| JP | 10-290777 | 11/1998 |
| WO | 99 42028 | 8/1999 |

OTHER PUBLICATIONS

Patent Abstracts of Japan, vol. 1995, No. 03, Apr. 28, 1995 & JP 06 331912 A (Sanyo Electric Co Ltd), Dec. 2, 1994.

* cited by examiner

Primary Examiner—John P. Leubecker
(74) Attorney, Agent, or Firm—Burr & Brown

(57) ABSTRACT

A body cavity-observing apparatus includes an endoscope with an imaging optical system on the front edge thereof, a prism movably mounted on the forefront of the imaging optical system, and an actuator to drive the prism on a given command signal. A different endoscope image is obtained by moving the prism, and thus, a wide range endoscope image can be easily obtained.

6 Claims, 4 Drawing Sheets

Light beam deflectable region

BODY CAVITY-OBSERVING APPARATUS

BACKGROUND OF THE INVENTION

1. Field of the Invention

This invention relates to a body cavity-observing apparatus for observing an internal organ or the like in the body cavity, including an endoscope with an imaging optical system at the forefront thereof to photograph an endoscope image.

2. Description of the Prior Art

Generally, endoscopes to be used in body cavities are classified as rigid endoscopes or fiberscopes. In order to obtain a different endoscope image by moving an endoscope, the rigid endoscope itself must be moved or the fiberscope itself must be moved or bent.

Recently, various endoscope manipulators in which endoscopes are installed have been developed. The endoscope manipulator can rapidly move the endoscope installed therein and obtain a different scope effectively. However, since the endoscope manupulator drives the conventional endoscope only actively, it may degrade the working property because of the movement or bending of the endoscope by an operator. Moreover, if the endoscope manupulator is operated mistakenly from a mistaken data input, the forefront of the endoscope may be made to approach an internal organ more than necessary.

In order to iron out the above conventional matters, the publications of unexamined patent applications Tokukai Hei 8-164148 (JP A 8-164148) and Tokukai Hei 10-290777 (JP A 10-290777) disclose scope-moving techniques. In the former publication, an endoscope follows a medical tool to obtain various endoscope image data on a wide-angle optical image, which are recorded in a memory. Then, the desired image data is selected from the recorded endoscope image data to control the scope of the endoscope. In the latter publication, all or a part of a super wide-angle optical image is displayed from a super wide-angle lens provided at the forefront of an endoscope to control the scope of the endoscope.

In the former case, since the recorded endoscope image data are based on the wide-angle optical image, each image data becomes very small, resulting in the degradation of the resolution and thus, the degradation of the endoscope image quality. In the latter case, if the part of the super wide-angle optical image is selected, the selected optical image also becomes very small, resulting in the degradation of the resolution and thus, the degradation of the endoscope image quality, as mentioned above. Moreover, since the super wide-angle optical lens provides more distorted images at the fringes than at the center, all of the wide-angle optical images cannot be practically provided.

SUMMARY OF THE INVENTION

It is an object of the present invention to provide a body cavity-observing apparatus which can provide various endoscope images of good quality without the movement or bending of an endoscope.

Therefore, this invention relates to a body cavity-observing apparatus comprising an endoscope with an imaging optical system on the front edge thereof, a prism movably mounted on the forefront of the imaging optical system, and an actuator to drive the prism on a given command signal, whereby a different endoscope image is obtained through the movement of the prism.

According to the body cavity-observing apparatus of the present invention, different endoscope images can be easily obtained by moving the prism without mechanical movement or mechanical bending of the endoscope itself. As a result, a wide range endoscope images can be easily obtained. Moreover, since only a given area directed by the prism is observed, the resolution of the thus obtained endoscope image can be enhanced. Furthermore, for example under a surgical operation, the working property and the safety of not approaching an internal organ more than necessary are improved.

In a preferred embodiment of the present invention, the prism includes first and second wedge prisms having the same vertical angle that are provided closely. The adjacent opposite surfaces are orthogonal to the optical axis of the wedge prisms. The actuator includes first and second outer tubes which are independently and movably attached to the first and the second wedge prisms, and first and second motors to rotate the first and the second wedge prisms around the optical axis, respectively. In this case, different endoscope images can be easily obtained through the independent rotations of the wedge prisms, and thus, a wide range endoscope image can be easily obtained.

In another preferred embodiment of the present invention, the prism includes one wedge prism. The actuator includes an outer tube movably provided on the periphery of the endoscope, a joining shaft to join the wedge prism and the outer tube, a first motor to tilt the wedge prism for the optical axis via the joining shaft and a second motor to rotate the wedge prism around the optical axis through the rotation of the outer tube. In this case, different endoscope images can be easily obtained through the rotation and tilt of the one wedge prism, and thus, a wide range endoscope image can be obtained.

In still another preferred embodiment of the present invention, the prism includes a liquid prism, and the actuator includes first and second link mechanisms which adjust the tilt angles for two directions orthogonal to the optical axis, respectively. The first and the second link mechanisms comprises pairs of link shafts composed of planar portions joined with the periphery of the liquid prism and orthogonal portions orthogonally followed by the planar portions, link members to support the orthogonal portions of the link shafts, and motors to rotate the link members. In this case, different endoscope images can be easily obtained through the backward and forward movement of the liquid prism, and thus, a wide range endoscope image can be easily obtained.

Moreover, it is desired that the link members each have elongated holes, respectively, and the link shafts are moved backward and forward by slipping the orthogonal portions in the elongated holes through the rotation of the link members by the motors.

In a further preferred embodiment of the present invention, a position-detecting means to detect the position of the prism is provided. An endoscope image is calibrated in its color aberration or distortion on the basis of the prism position information from the position-detecting means. Therefore, the resolution of the endoscope image can be more enhanced.

BRIEF DESCRIPTION OF THE DRAWINGS

For better understanding of the present invention, reference is made to the attached drawings, wherein.

DETAILED DESCRIPTION OF THE INVENTION

Figure 1:
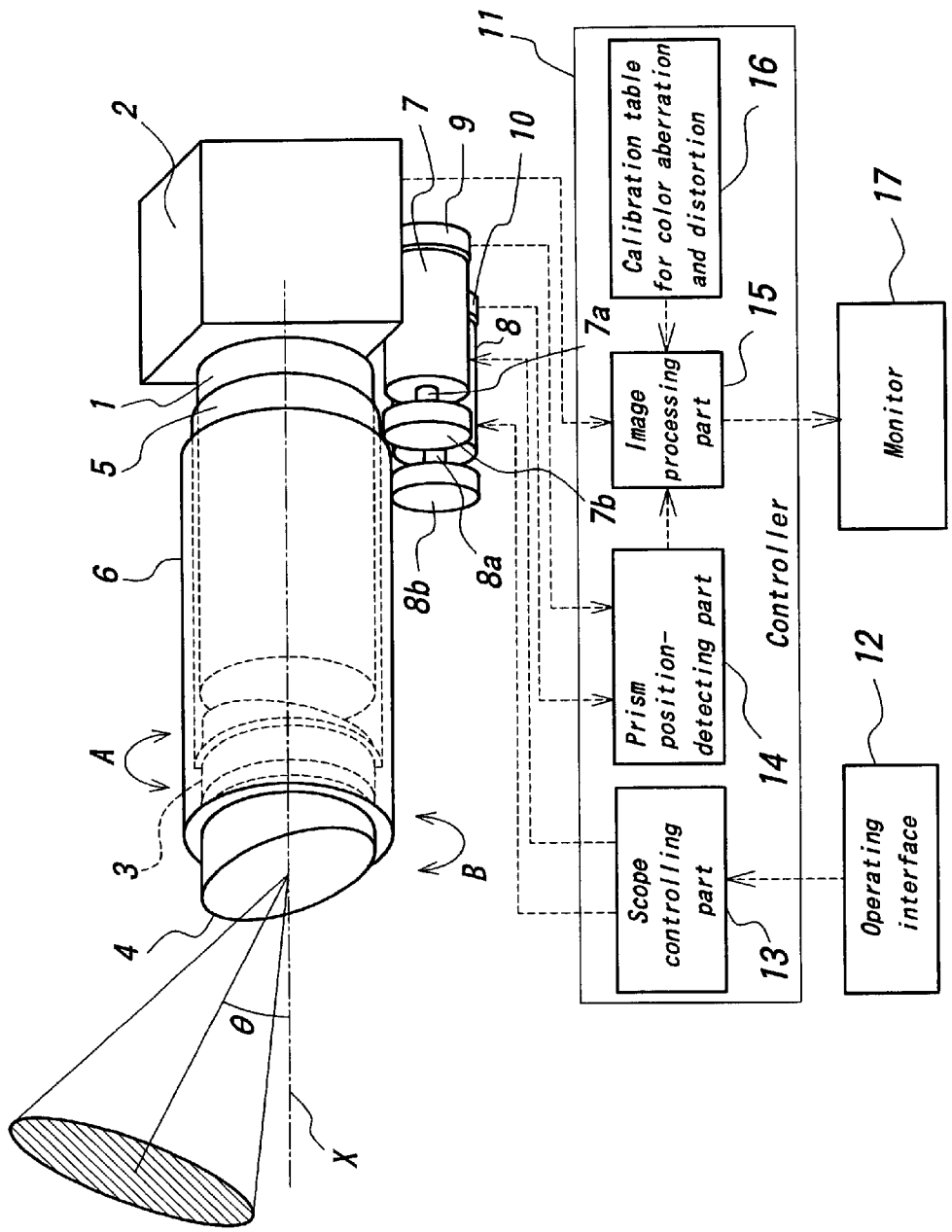
FIG. 1 is a schematic view showing the entire structure of a body cavity-observing apparatus according to the present invention.

This invention will be described in detail with reference to figures. FIG. 1 is a schematic view showing the entire structure of a body cavity-observing apparatus according to the present invention. The depicted body cavity-observing apparatus has, as an endoscope, a rigid endoscope 1 having about 10 mm diameter in the part to be inserted and about 300 mm entire length. Moreover, the endoscope may be constructed of a fiberscope.

Figure 2A:
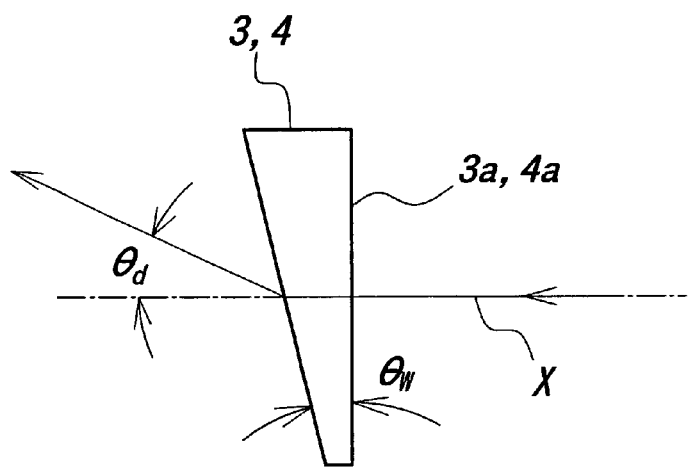
FIGS. 2(a)–2(c) are explanatory views for the principle of the bending of an optical axis using a wedge prism in the body cavity-observing apparatus shown in FIG. 1.
Figure 2B:
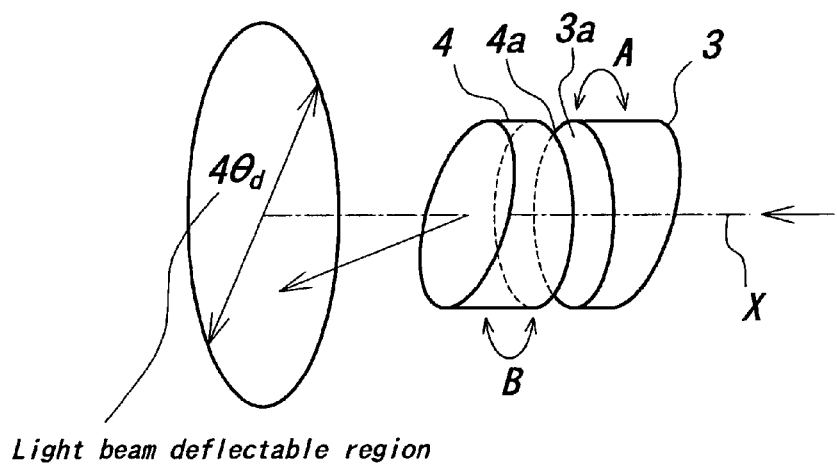
Figure 2C:
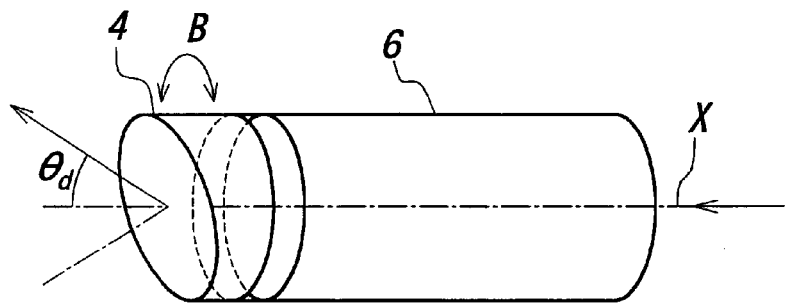

A CCD camera 2 is provided, as an imaging means, in the right side of FIG. 1. Herein, if a zoom mechanism is added, it is provided between the rigid endoscope 1 and the CCD camera 2. Moreover, an imaging optical system (not shown) to photograph an endoscope image is mounted at the forefront of the rigid endoscope 1 (in the left side of FIG. 1). First and second wedge prisms 3 and 4 to constitute a prism means are attached to the forefront of the imaging optical system movably. The wedge prisms 3 and 4 have the same wedge vertical angle θw as shown in FIG. 2(a), and are positioned closely so that their first surfaces 3a and 4a perpendicular to the optical axis X are opposed each other as shown in FIG. 2(b).

The wedge prisms 3, 4 and the rigid endoscope 1 are covered doubly with first and second outer tubes 5 and 6, which are independently movable. At the right side edges of the outer tubes 5 and 6 are attached gears (not shown), to which gears 7b and 8b to be joined with the forefronts of the rotation shafts 7a and 8a of first and second motors 7 and 8 are checked. Rotary encoders 9 and 10 to detect the motor driving amount (rotation number) are joined with the right side edges of the motors 7 and 8. The outer tubes 5, 6 and the motors 7 and 8 constitute an actuator to drive the wedge prisms 3 and 4.

A controller 11 to control the driving amounts of the motors 7 and 8 is provided. A command signal from an operating interface 12 controlled by an operator is input to the controller, as well as the driving amounts of the motors 7 and 8 detected by the rotary encoders 9 and 10, and an endoscope image from the CCD camera 2. The controller 11 has a scope controlling part 13 to control the driving amounts of the motors 7 and 8 based on the command signal from the operating interface 12, and a prism position-detecting part 14 to detect the movement positions of the wedge prisms 3 and 4 based on the driving amounts of the motors 7 and 8 detected by the rotary encoders 9 and 10.

Moreover, the controller 11 has a calibration table 16 for color aberration and distortion, and an image processing part 15 to calibrate the color aberration and distortion of an endoscope image detected by the CCD camera 2 based on the calibration table 16. In this case, a monitor 17 may be prepared so that the endoscope image can be observed.

The controller 11, the operating interface 12 and the monitor 17 may be constructed of a general-purpose computer, for example. In this case, the scope controlling part 13, the prism position-detecting part 14 and the image processing part 15 of the controller 11 may be constructed from given software installed in the computer, and the calibration table 16 of the controller 11 may be constructed of the data recorded in a memory (RAM, ROM, hard disk, etc.) in the computer. Moreover, the operating interface 12 may be constructed of the keyboard or the mouse of the computer. The scope controlling part 13, the prism position-detecting part 14 and the image processing part 15 may be constructed of other devices, and the image processing part 15 may be made of a hardware member, such as an image processing board.

The scope controlling operation using the above body cavity-observing apparatus will be described hereinafter.

When a command signal to follow an object to be observed is input into the scope controlling part 13 from the operating interface 12, the driving amounts of the motors 7 and 8 are determined by the scope controlling part 13, to drive the motors 7 and 8 by the determined driving amounts. Then, the wedge prisms 3 and 4 are rotated independently by the motors 7 and 8 in the directions designated by the arrows A and B via the rotation shafts 7a and 8a, the gears 7b and 8b, and the outer tubes 5 and 6. As a result, the prisms 3 and 4 are moved to different positions from their respective starting positions.

Providing that a light beam is introduced along the optical axis X onto the first surface 4a of the wedge prism 4 perpendicular to the optical axis X, the relation between the wedge vertical angle θw of the wedge prism 4 and the light beam polarizing angle θd is represented by the following equation:

$$\theta d = \arcsin(n \sin \theta w) - \theta w \qquad (1)$$

Herein, reference character "n" designates the refractive index of the wedge prism 4.

Therefore, the endoscope image in the θd direction can be observed by the wedge prism 4 movably attached at the forefront of the rigid endoscope 1. If the wedge prism 4 is rotated around the optical axis X of the rigid endoscope 1, the endoscope image within the region of the θd direction around the optical axis X can be observed.

Moreover, if the adjacent two wedge prisms 3 and 4 are rotated independently in the directions of the arrows A and B around the optical axis X, the light beam can be deflected in a given direction within a conical shape defined by the wedge prisms 3 and 4. The maximum deflection angle is a half of the vertical angle of the conical shape, and is almost defined as 2θd if the vertical angles of the wedge prisms 3 and 4 are very small. Therefore, the light beam can be deflected within a region of 4θd by the wedge prisms 3 and 4, as shown in FIG. 2(b).

As a result, in the above body cavity-observing apparatus according to the present invention in which the two wedge prisms 3 and 4 are provided closely and rotated independently, the deflecting condition of the light beam from the optical axis X is controlled on the basis of the command signal from the operating interface 12, and a different endoscope image can be obtained within the 4θd region.

In observing the different endoscope images through the movement of the wedge prisms 3 and 4, the observed endoscope images may be distorted to some degree due to the incident angle of the light beam, the angle of the incident surface of the wedge prisms and the distance of the light beam from the optical axis X. Moreover, since the refractive indexes n of the wedge prisms are vary with the wavelength of the light beam, the observed endoscope image has color aberration therein. The degree of the distortion and the color aberration of the endoscope image can be obtained from the calculation or the calibration, depending on the positions of the wedge prisms when they are rotated around the optical axis X, and thus, in this embodiment, stored in the calibration table 16 of the controller 11.

In the above controller 11, as mentioned above, the rotary encoders 9 and 10 as position-detecting means detect the driving amounts of the motors 7 and 8, and the positions of the wedge prisms 3 and 4 to define the endoscope image are measured on the driving amounts. Then, the calibrations for the color aberration and the distortion of the endoscope image related to the positions of the wedge prisms are determined from the calibration table 16. Subsequently, the endoscope image is calibrated in its color aberration and the distortion by the image processing part 15 on the measured color aberration calibration and distortion calibration, and is displayed on the monitor 17. If the color aberration or the distortion is very small and negligible, the calibration for the one may be omitted.

In the above body cavity-observing apparatus, only if a given command signal is input into the operating interface 12, the wedge prisms 3 and 4 are rotated to their respective positions and thus, a different endoscope image can be obtained from the movement of the wedge prisms 3 and 4. Therefore, under a surgical operation, the working property can be developed and the forefront of the endoscope cannot be made to approach an internal organ more than necessary.

Moreover, since only a given area directed by the wedge prisms 13 and 14 is observed, the resolution of the endoscope image can be enhanced. As a result, the quality of the endoscope image can be improved. Moreover, since the endoscope image is calibrated in its color aberration and distortion on the calibration table 16, the quality of the endoscope image can be more enhanced.

Figure 3:
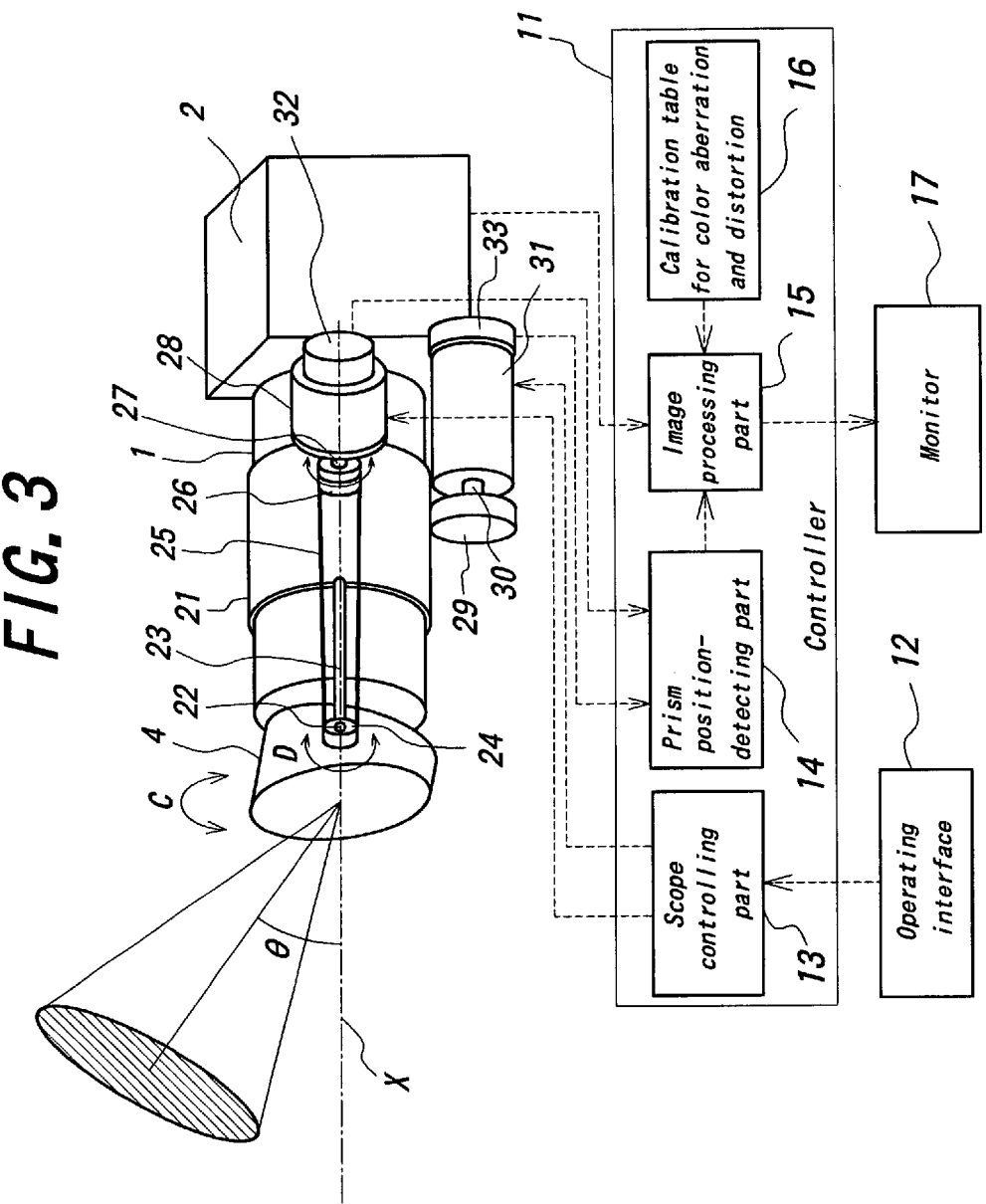
FIG. 3 is a schematic view showing the entire structure of another body cavity-observing apparatus according to the present invention.

FIG. 3 is a schematic view showing the entire structure of another body cavity-observing apparatus according to the present invention. Compared with the body cavity-observing apparatus shown in FIG. 1, the body cavity-observing apparatus has only one wedge prism. Therefore, the actuator is modified so as to adapt to the one wedge prism. The other parts are similar to the parts of FIG. 1, and the same reference characters are given to similar parts.

In the body cavity-observing apparatus shown in FIG. 3, the only one wedge prism 4 is attached to the forefront of the not shown imaging optical system provided at the left edge of the rigid endoscope 1, so that the right-handed surface is perpendicular to the optical axis. The above-mentioned actuator is constructed of an outer tube 21 movably provided on the periphery of the rigid endoscope 1, a joining shaft 23 to join the wedge prism 4 and the outer tube 21 via a rotation shaft 22, a pulley 24 joined with the forefront of the rotation shaft 22, a belt 25 associated with the pulley 24, a pulley 26 provided on the outer tube 21, a first motor 28 having a rotation shaft 27 joined with the pulley 26, and a second motor 31 having a gear 29 joined via a rotation shaft 30.

Then, another rotation shaft 22, another joining shaft 23 and another pulley 24 are provided on the back side of the body cavity-observing apparatus so as to oppose the rotation shaft 22, the joining shaft 23 and the pulley 24 which are provided on the front side thereof. That is, the wedge prism 4 is sandwiched by the pair of rotation shafts 22, the pair of joining shafts 23 and the pair of pulleys 24.

Next, the scope controlling operation using the above body cavity-observing apparatus shown in FIG. 3 will be described hereinafter. When a command signal to follow an object to be observed is input into the scope controlling part 13 from the operating interface 12, the driving amounts of the motors 28 and 31 are determined by the scope controlling part 13, to drive the motors 28 and 31 by the determined driving amounts. Then, the wedge prism 4 is rotated in the direction designated by the arrow C around the optical axis X by the motor 31 via the rotation shaft 30, the gear 29, the outer tube 21, the joined shaft 23 and the rotation shaft 22.

At the same time, the wedge prism 4 is rotated by a given angle in the direction designated by the arrow D around the rotation shaft 22 by the motor 28 via the rotation shaft 27, the pulley 26, the belt 25 and the pulley 24. As a result, the prism 4 is moved to a different position from its starting position.

In the body cavity-observing apparatus shown in FIG. 3, the only one wedge prism is rotated in the arrow C direction and tilted in the arrow D direction, instead of independently rotating the wedge prisms 3 and 4 as mentioned in FIG. 1. Therefore, in this case, a different endoscope image can be obtained from the movement of the wedge prism 4. As a result, under a surgical operation, the working property can be developed and the forefront of the endoscope cannot be made to approach an internal organ more than necessary. Moreover, the resolution of the endoscope image can be enhanced. In this case, the endoscope image can be also calibrated in its color aberration and distortion on the calibration table 16.

Figure 4:
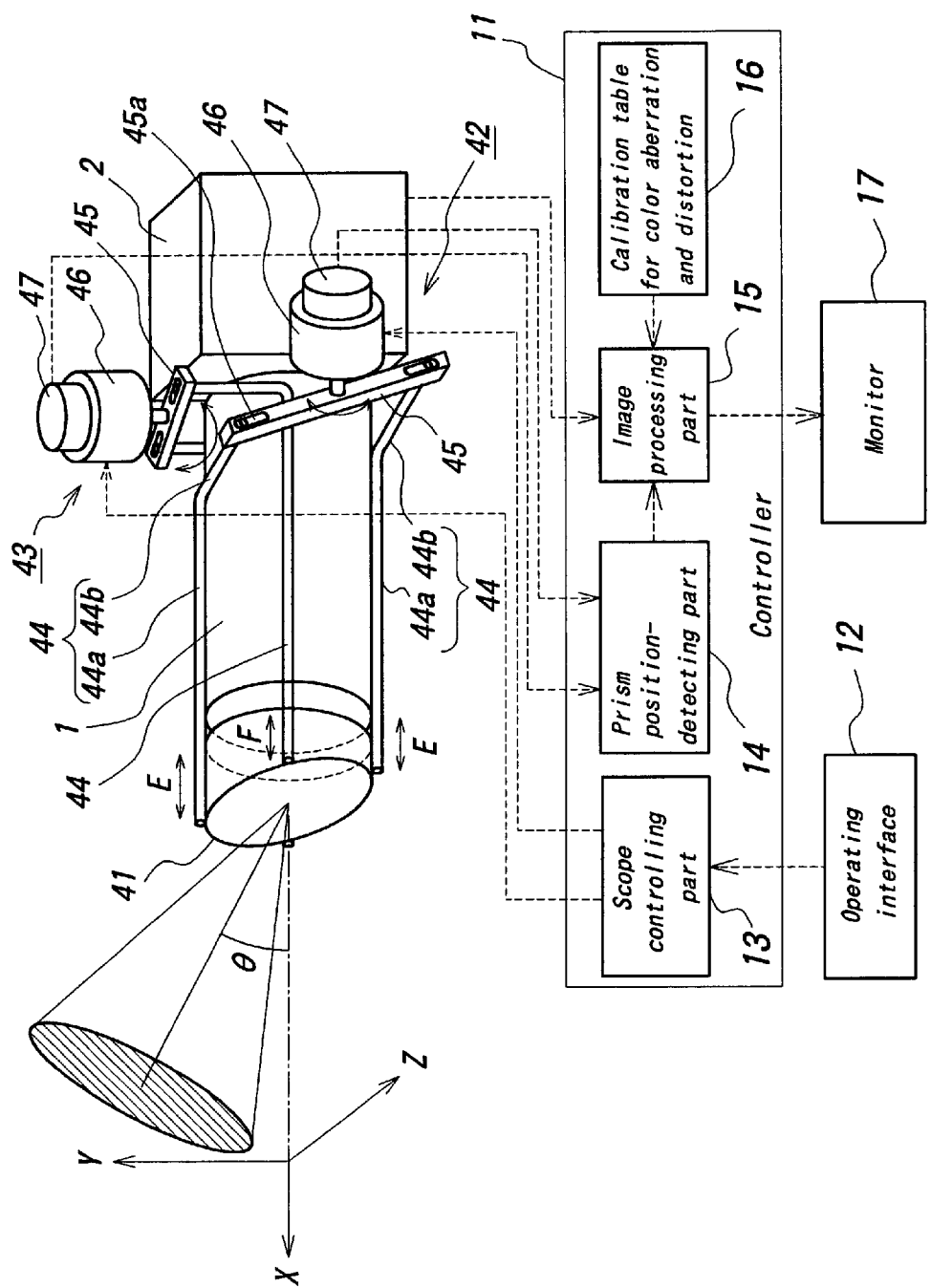
FIG. 4 is a schematic view showing the entire structure of still another body cavity-observing apparatus according to the present invention.

FIG. 4 is a schematic view showing the entire structure of still another body cavity-observing apparatus according to the present invention. Compared with the body cavity-observing apparatus shown in FIG. 3, a liquid prism is employed instead of the wedge prism, and an actuator to move the liquid prism backward and forward along the optical axis X is provided. The other parts are similar to the ones in FIG. 3, and the same reference characters are given to similar parts.

In the body cavity-observing apparatus shown FIG. 4, the liquid prism 41 is attached to the forefront of the not shown imaging optical system provided at the left edge of the rigid endoscope 1, so that the right-handed surface is perpendicular to the optical axis X. The actuator is constructed of a first and a second link mechanisms 42 and 43 which adjust the tilt angles for the Y-axis and the Z-axis orthogonal to the X-axis.

The link mechanisms 42 and 43 have pairs of link shafts 44 composed of planar portions 44a joined with the periphery of the liquid prism 41 and orthogonal portions 44b orthogonally followed by the planar portions 44a, link members 45 to support the orthogonal portions 44b of the link shafts 44, and motors 46 to rotate the link members 45 around the Y axis and Z axis, respectively. The link members 45 have elongated holes 45a, respectively, and the link shafts 44 are moved backward and forward by slipping the orthogonal portions 44b in the elongated holes 45a through the rotation of the link members 45 by the motors 46. Then, rotary encoders 47 to count the rotation numbers of the motors 46 are attached on the motors 46, respectively.

Next, the scope controlling operation using the body cavity-observing apparatus shown in FIG. 4 will be described hereinafter. When a command signal to follow an object to be observed input into the scope controlling part 13 from the operating interface 12, the driving amounts of the motors 46 are determined by the scope controlling part 13, to drive the motors 46 by the determined driving amounts. Then, the link mechanisms 42 and 43 are moved backward and forward along the X axis by the motors 46, to move the liquid prism 41 backward and forward in the directions designated by the arrows E and F shown in FIG. 4. Therefore, the forefront surface (left-handed surface) of the liquid prism 41 is tilted by a given angle. As a result, the liquid prism 41 is moved at its different position from its starting position without the mechanical movement or bending of the rigid endoscope.

In the body cavity-observing apparatus shown in FIG. 4, the only one liquid prism 41 is moved backward and forward in the arrows E and F directions, instead of rotating in the arrow C direction around the optical axis X and tilting in the arrow D direction the only one wedge prism 4 as mentioned in FIG. 3. Therefore, in this case, a different endoscope image can be obtained from the forward and backward movement of the liquid prism 41. As a result, under a surgical operation, the working property can be developed and the forefront of the endoscope cannot be made to approach an internal organ more than necessary. Moreover, the resolution of the endoscope image can be enhanced. In this case, the endoscope image can be also calibrated in its color aberration and distortion on the calibration table 16.

As is apparent from the above description, since a different endoscope image can be easily obtained by slightly driving the wedge prism or the liquid prism movably mounted on the forefront of the rigid endoscope, for example, a wide range endoscope image can be easily obtained and the body cavity-observing apparatus can be miniaturized. Moreover, due to the slight movement of the prism, the forefront of the rigid endoscope cannot be made to approach an internal organ more than necessary even if the actuator is operated mistakenly.

If a zoom mechanism is mounted on the above body cavity-observing apparatus, the magnification and reduction of the endoscope images can be also carried out by a given optical system for the zoom mechanism, in addition to the above-mentioned optical system such as the rigid endoscope and the prism to obtain a different endoscope image, and thus, a wide range endoscope image. Therefore, since the body cavity-observing apparatus does not itself require mechanical bending or mechanical movement, the working property or the safety of not making an approach to an internal organ more than necessary can be developed under a surgical operation.

Although the present invention was described in detail with reference to the above examples, this invention is not limited to the above disclosure and every kind of variation and modification may be made without departing from the scope of the present invention.

What is claimed is:

1. A body cavity-observing apparatus, comprising:
    an endoscope having an imaging optical system on a front edge thereof;
    a prism unit movably mounted on a front edge of said imaging optical system;
    an actuator to drive said prism unit on a given command signal; and
    a position-detecting means to detect a position of said prism unit;
    whereby an endoscope image is calibrated in its color aberration or distortion based on prism unit position information and a different endoscope image is obtained through movement of said prism unit.

2. The body cavity-observing apparatus defined in claim 1, wherein said prism unit comprises one wedge prism; and
    said actuator comprises an outer tube movably provided on a peripheral portion of said endoscope, a joining shaft to join said wedge prism and said outer tube, a first motor to tilt said wedge prism toward an optical axis via said joining shaft and a second motor to rotate said wedge prism around said optical axis through the rotation of said outer tube;
    whereby the different endoscope image is obtained through the rotation and tilt of said one wedge prism.

3. The body cavity-observing apparatus defined in claim 1, wherein said prism unit further comprises a liquid prism; and
    said actuator further comprises a first link mechanism and a second link mechanism which adjust the tilt angles for two directions orthogonal to the optical axis, respectively, said first and said second link mechanisms each comprising a pair of link shafts composed of planar portions joined with a peripheral portion of said liquid prism and orthogonal portions orthogonally followed by said planar portions, link members to support said orthogonal portions of said link shafts, and motors to rotate said link members;
    whereby the different endoscope image is obtained through the backward and forward movement of said liquid prism.

4. The body cavity-observing apparatus defined in claim 3, wherein each said link member further comprises elongated holes, and said link shafts are moved backward and forward by slipping said orthogonal portions in said elongated holes through the rotation of said link members by said motors.

5. A body cavity-observing apparatus comprising an endoscope having an imaging optical system on a front edge thereof;
    a prism unit movably mounted on a front edge of said imaging optical system, said prism unit comprising a first wedge prism and a second wedge prism, said first and said second wedge prisms having the same vertical angle, said first and said second wedge prisms being provided closely and said first and second wedge prisms having adjacent opposite surfaces orthogonal to an optical axis of each said first and second wedge prism; and
    an actuator to drive said prism unit on a given command signal, said actuator comprising a first outer tube and a second outer tube, said first and said second outer tubes being attached independently and movably to said first and said second wedge prisms, and a first motor and a second motor to rotate said first and said second wedge prisms around said optical axis, respectively;
    whereby a different endoscope image is obtained through independent rotation of said first and said second wedge prisms.

6. The body cavity-observing apparatus defined in claim 5, further comprising a position-detecting means to detect a position of said prism unit, whereby an endoscope image is calibrated in its color aberration or distortion on the basis of prism unit position information.

* * * * *